United States Patent
Kan et al.

(10) Patent No.: US 11,147,881 B2
(45) Date of Patent: *Oct. 19, 2021

(54) CONTROLLED DRUG RELEASE LIPOSOME COMPOSITIONS AND METHODS THEREOF

(71) Applicants: TAIWAN LIPOSOME COMPANY, LTD., Taipei (TW); TLC BIOPHARMACEUTICALS, INC., South San Francisco, CA (US)

(72) Inventors: Pei Kan, Taipei (TW); Yun-Long Tseng, Taipei (TW); Han-Chun Ou, Taipei (TW); Chun-yen Lai, Taipei (TW)

(73) Assignees: Taiwan Liposome Company, Ltd., Taipei (TW); TLC Biopharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/241,617

(22) Filed: Jan. 7, 2019

(65) Prior Publication Data

US 2019/0216932 A1 Jul. 18, 2019

Related U.S. Application Data

(63) Continuation of application No. 15/610,163, filed on May 31, 2017, now Pat. No. 10,220,095, which is a
(Continued)

(51) Int. Cl.
*A61K 47/36* (2006.01)
*A61K 9/127* (2006.01)
(Continued)

(52) U.S. Cl.
CPC .............. *A61K 47/36* (2013.01); *A61K 9/127* (2013.01); *A61K 9/1271* (2013.01);
(Continued)

(58) Field of Classification Search
CPC ..................................................... A61K 9/127
See application file for complete search history.

(56) References Cited

U.S. PATENT DOCUMENTS

| | | | | |
|---|---|---|---|---|
| 5,192,549 A | * | 3/1993 | Barenolz | A61K 9/1278 264/4.1 |
| 5,316,771 A | | 5/1994 | Barenholz et al. | |

(Continued)

FOREIGN PATENT DOCUMENTS

| | | |
|---|---|---|
| CN | 1771954 | 5/2006 |
| CN | 1839800 | 10/2006 |

(Continued)

OTHER PUBLICATIONS

JN Israelachvili, S Marcelja, RG Horn. "Physical principles of membrane organization." Quarterly Reviews of Biophysics, vol. 13(2), 1980, pp. 121-200. (Year: 1980).*

(Continued)

*Primary Examiner* — Isaac Shomer

(74) *Attorney, Agent, or Firm* — Finnegan, Henderson, Farabow, Garrett & Dunner, LLP

(57) ABSTRACT

The present invention relates to pharmaceutical compositions comprising at least one liposome, at least one polyvalent counterion donor or a pharmaceutically acceptable salt thereof, at least one monovalent counterion donor or a pharmaceutically acceptable salt thereof, and an amphipathic therapeutic agent or a derivative or pharmaceutically acceptable salt thereof. The present invention also relates to methods of inhibiting cancer cell growth while reducing toxicity, comprising administering the pharmaceutical composition described herein.

3 Claims, 4 Drawing Sheets

Skin toxicity evaluation in liposomal VNB treated scid mice

Related U.S. Application Data continuation-in-part of application No. 14/774,833, filed as application No. PCT/US2014/029907 on Mar. 15, 2014, now Pat. No. 9,700,511.

(60) Provisional application No. 61/792,850, filed on Mar. 15, 2013.

(51) Int. Cl.

| | | |
|---|---|---|
| A61K 47/02 | (2006.01) | |
| A61K 31/475 | (2006.01) | |
| A61K 31/4745 | (2006.01) | |
| A61K 31/365 | (2006.01) | |
| A61K 31/704 | (2006.01) | |
| A61K 31/337 | (2006.01) | |
| A61K 31/7048 | (2006.01) | |

(52) U.S. Cl.
CPC .......... *A61K 31/337* (2013.01); *A61K 31/365* (2013.01); *A61K 31/475* (2013.01); *A61K 31/4745* (2013.01); *A61K 31/704* (2013.01); *A61K 31/7048* (2013.01); *A61K 47/02* (2013.01)

(56) References Cited

U.S. PATENT DOCUMENTS

| | | | |
|---|---|---|---|
| 8,765,181 | B2 | 7/2014 | Liang et al. |
| 9,700,511 | B2 * | 7/2017 | Kan ............... A61K 31/475 |
| 10,220,095 | B2 * | 3/2019 | Kan ............... A61K 9/1271 |
| 2001/0051183 | A1 | 12/2001 | Martin et al. |
| 2002/0146450 | A1 * | 10/2002 | Slater ............... A61K 31/473 424/450 |
| 2003/0082228 | A1 | 5/2003 | Flowers et al. |
| 2004/0170677 | A1 | 9/2004 | Hu et al. |
| 2005/0232984 | A1 | 10/2005 | Haas et al. |
| 2006/0051406 | A1 | 3/2006 | Parmar |
| 2006/0165744 | A1 | 7/2006 | Jamil et al. |
| 2007/0116753 | A1 * | 5/2007 | Hong ............... A61K 31/337 424/450 |
| 2007/0122414 | A1 | 5/2007 | Georges et al. |
| 2009/0081121 | A1 | 3/2009 | Ting et al. |
| 2012/0171283 | A1 | 7/2012 | Hong et al. |
| 2016/0235671 | A1 | 8/2016 | Li et al. |
| 2016/0310600 | A1 | 10/2016 | Ali et al. |
| 2017/0224715 | A1 | 8/2017 | Hayes et al. |

FOREIGN PATENT DOCUMENTS

| | | | |
|---|---|---|---|
| CN | 101849915 | | 10/2006 |
| CN | 1980637 | | 6/2007 |
| CN | 100998562 | | 7/2007 |
| CN | 101129375 | | 2/2008 |
| CN | 101843584 | | 9/2010 |
| CN | 101933904 | | 1/2011 |
| EP | 1959961 | A2 | 8/2008 |
| EP | 2262369 | A1 | 12/2010 |
| WO | WO-0066126 | A2 * | 11/2000 ........... A61K 9/1278 |
| WO | WO-2003/018018 | A2 | 3/2003 |
| WO | WO-2004/105782 | A2 | 12/2004 |
| WO | WO-2005/107712 | A1 | 11/2005 |
| WO | WO-2007/049278 | A2 | 5/2007 |
| WO | WO 2007/111720 | A2 | 10/2007 |
| WO | WO 2009/123595 | A1 | 10/2009 |
| WO | WO-2010092590 | A2 * | 8/2010 ............. A61K 31/65 |
| WO | WO-2011/092708 | A2 | 8/2011 |
| WO | WO 2014/121211 | A2 | 8/2014 |
| WO | WO 2017/053464 | A1 | 3/2017 |
| WO | WO 2017/097196 | A1 | 6/2017 |

OTHER PUBLICATIONS

Stephen Dealler & Nikolai G Rainov. "Pentosan polysulfate as a prophylactic and therapeutic agent against prion disease." IDrugs, vol. 6(5), 2003, pp. 470-478. (Year: 2003).*

E. V. Tazina, K. V. Kostin, and N. A. Oborotova. "Drug Synthesis Methods and Manufacturing Technology—Specific Features of Drug Encapsulation in Liposomes (a Review)." Pharmaceutical Chemistry Journal, vol. 45, No. 8, Nov. 2011, pp. 481-490. (Year: 2011).*

CAS Registry Record for Irinotecan (Cas# 97682-44-5). Entered STN Aug. 18, 1985, downloaded Apr. 14, 2016, 2 printed pages.

Drummond, et al. Improved Pharmacokinetics and Efficacy of a Highly Stable Nanoliposomal Vinorelbine, JPET 328:321-330, 2009.

Harasym, et al. Sphingomyelin-cholesterol liposomes significantly enhance the pharmacokinetic and therapeutic properties of vincristine in murine and human tumour models, British Journal of Cancer (1995) 72, 896-904.

Johnston, et al. Therapeutically optimized rates of drug release can be achieved by varying the drug-to-lipid ratio in liposomal vincristine formulations; Biochimica et Biophysica Acta 1758 (2006) 55-64.

Rao, et al. Pharmacokinetics, efficacy and toxicity of different pegylated liposomal doxorubicin formulations in preclinical models: is a conventional bioequivalence approach sufficient to ensure therapeutic equivalence of pegylated liposomal doxorubicin products? Cancer Chemother Pharmacal (201 0) 66:1173-1184.

Semple, et al. Optimization and Characterization of a Sphingomyelin/Cholesterol Liposome Formulation of Vinorelbine with Promising Antitumor Activity; Journal of Pharmaceutical Sciences, vol. 94, No. 5, May 2005.

Zhang, et al. A lipid microsphere vehicle for vinorelbine: Stability, safety and pharmacokinetics, International Journal of Pharmaceutics 348 (2008) 70-79.

Zhigaltsev, et al. Liposome-encapsulated vincristine, vinblastine and vinorelbine: A comparative study of drug loading and retention; Journal of Controlled Release 104 (2005) 103-111.

Zhigaltsev, et al. Formation of drug-arylsulfonate complexes inside liposomes: A novel approach to improve drug retention; Journal of Controlled Release 110 (2006) 378-386.

Zhu, et al, "The effect of vincristine-polyanion complexes in STEALTH liposomes on pharmacokinetics, toxicity and anti tumor activity." Cancer Chemotherapy and Pharmacology, vol. 39, 1996, pp. 138-142.

Russian Patent Application No. 2015135629, Office Action dated Mar. 6, 2018, 13 pages.

Mashovsky, M.D., "Lekarstvennye Sredstva," 16th edition, Publisher: Umerenkov, 3 pages (2012).

* cited by examiner

CONTROLLED DRUG RELEASE LIPOSOME COMPOSITIONS AND METHODS THEREOF

CROSS REFERENCE TO RELATED APPLICATIONS

This application is a continuation of U.S. application Ser. No. 15/610,163, filed May 31, 2017, which is a continuation-in-part of U.S. application Ser. No. 14/774,833, filed Sep. 11, 2015, which is a national stage entry of International Application No. PCT/US2014/029907, filed Mar. 15, 2014, which claims the benefit of U.S. Provisional Application No. 61/792,850, filed Mar. 15, 2013, the entire disclosures of which are incorporated herein by reference.

TECHNOLOGY FIELD

The present invention relates to a pharmaceutical composition comprising at least one liposome, at least one polyvalent counterion donor or a pharmaceutically acceptable salt thereof, at least one monovalent counterion donor or a pharmaceutically acceptable salt thereof, and a therapeutic agent or a derivative or pharmaceutically acceptable salt thereof.

BACKGROUND OF THE INVENTION

Liposomes have been widely used as an in vivo carrier of various therapeutic agents. Ideally, such liposomes should have a high encapsulating efficiency and an extended retention profile (i.e., minimal release of the drug before reaching the targeted site).

NanoVNB® is a liposomal vinorelbine product, which utilizes liposomes to enhance the retention of vinorelbine before it reaches the targeted site. A Phase I clinical trial of NanoVNB® showed enhanced anti-cancer efficacy, but the extended retention of vinorelbine in vivo also led to increased toxicity.

Therefore, there is a need to provide a liposomal composition that is useful for delivery of a therapeutic agent with an adjustable retention profile, and to obtain a balance between optimal anti-cancer efficacy and minimal side effects. The present invention addresses this need, as well as other important needs.

BRIEF SUMMARY OF THE INVENTION

In one embodiment, the present invention is directed to a pharmaceutical composition comprising at least one liposome, at least one polyvalent counterion donor or a pharmaceutically acceptable salt thereof, at least one monovalent counterion donor or a pharmaceutically acceptable salt thereof, and a therapeutic agent, a derivative thereof, or a pharmaceutically acceptable salt thereof. Advantageously, this pharmaceutical composition provides an adjustable retention profile and an adjustable encapsulation percentage of the therapeutic agent.

In another embodiment, the present invention provides a pharmaceutical composition, comprising at least one liposome having a particle-forming component selected from a phospholipid or a mixture of at least one phospholipid and cholesterol; 0.1 mM to 10 mM polyvalent counterion donor or a pharmaceutically acceptable salt thereof; 150 mM to 450 mM monovalent counterion donor or a pharmaceutically acceptable salt thereof; and a vinca alkaloid.

In another embodiment, the present invention provides a pharmaceutical composition, comprising at least one liposome having a particle-forming component selected from a phospholipid or a mixture of at least one phospholipid and cholesterol; 1 milliequivalent per liter (mEq/L) to 320 mEq/L polyvalent counterion donor or a pharmaceutically acceptable salt thereof, on the basis of total volume of the pharmaceutical composition; 150 mM to 450 mM monovalent counterion donor or a pharmaceutically acceptable salt thereof; and an amphipathic therapeutic agent. The amount of the polyvalent counterion donor or a pharmaceutically acceptable salt thereof is adjustable upon the valency of a polyvalent counterion donor and the molar concentration of the polyvalent counterion donor.

The present invention is also directed to methods of inhibiting cancer cell growth in a subject in need thereof. The method comprises administering a pharmaceutical composition described herein, wherein the symptoms and signs of cancer in the subject are significantly reduced. Advantageously, this method enhances cancer cell inhibition and reduces toxicity significantly when compared with administration of a pharmaceutical composition comprising i) a liposome, ii) either but not both a monovalent counterion donor or a polyvalent counterion donor (or a pharmaceutically acceptable salt thereof), and iii) a therapeutic agent or derivative or pharmaceutically acceptable salt thereof.

Statements containing these terms should be understood not to limit the subject matter described herein or to limit the meaning or scope of the patent claims below. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description that follow.

DETAILED DESCRIPTION OF THE INVENTION

Definitions

Figure 1:
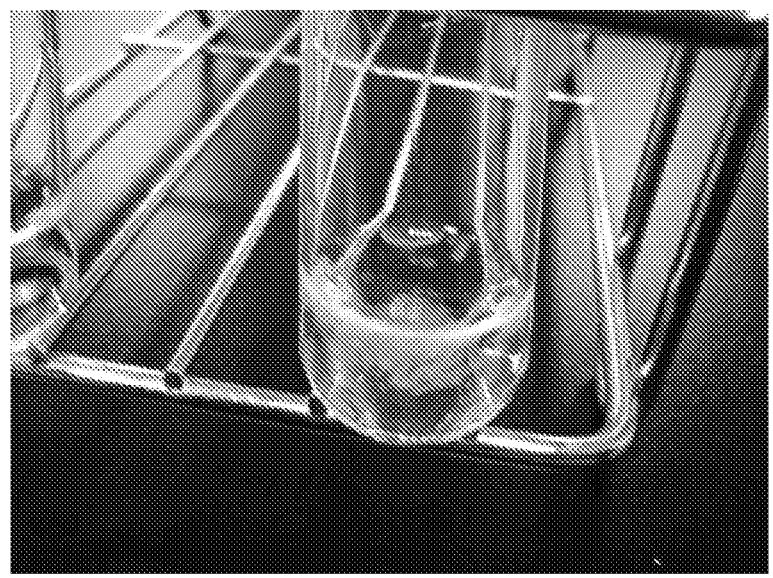
FIG. 1 shows precipitation of sodium dextran sulfate and vinorelbine in the liposome.

As employed above and throughout the disclosure, the following terms, unless otherwise indicated, shall be understood to have the following meanings.

As used herein, the singular forms "a," "an," and "the" include the plural reference unless the context clearly indicates otherwise.

An "effective amount," as used herein, includes a dose of the pharmaceutical composition that is sufficient to reduce the symptoms and signs of cancer, which include, but are not limited to, weight loss, pain and tumor mass, which is detectable, either clinically as a palpable mass or radiologically through various imaging means.

The term "treating," "treated," or "treatment" as used herein includes preventative (e.g., prophylactic), palliative, and curative uses or results.

The term "inhibiting" and "suppressing" includes slowing or stopping the growth of a tumor.

The term "subject" can refer to a vertebrate having cancer or to a vertebrate deemed to be in need of cancer treatment. Subjects include warm-blooded animals, such as mammals, including primates, and, more preferably, humans. Non-human primates are subjects as well. The term subject includes domesticated animals, such as cats, dogs, livestock (for example, cattle, horses, pigs, sheep, goats, etc.) and laboratory animals (for example, mice, rabbits, rats, gerbils, guinea pigs, etc.). Thus, veterinary uses and medical formulations are contemplated herein.

The term "counterion donor" means an ion or charged compound capable of forming a salt with a therapeutic agent and which does not reduce the activity of the therapeutic agent. In one embodiment, the therapeutic agent is an amphipathic acid with a net negative charge, and the counterion donor is a cationic ion or an entity covalently linked to one or more cationic functional groups. In another embodiment, the therapeutic agent is an amphipathic base with a net positive charge, and the counterion donor is an anionic ion or an entity covalently linked to one or more anionic functional groups. The counterion donor has high solubility in the agent-carrying component of the liposome, but a low penetration ability through the liposome membrane (bilayer). Therefore, the counterion donor is retained in the agent-carrying component during loading of the therapeutic agent, and during storage. In some embodiments, the pharmaceutical composition comprises a pharmaceutically acceptable salt of the counterion donor. In one such embodiment, the pharmaceutically acceptable salt comprises a positively-charged counterion donor and one or more anionic ions. In another such embodiment, the pharmaceutically acceptable salt comprises a negatively-charged counterion donor and one or more cationic ions.

Counterion donors may be monovalent counterion donors or polyvalent counterion donors. The term "monovalent" counterion donor describes a counterion donor comprising at least one ion or comprising one charged functional group covalently linked to an entity. Monovalent counterion donors may be at least one anionic ion, at least one cationic ion, an entity covalently linked to one anionic functional group, or an entity covalently linked to one cationic functional group. The term "polyvalent" counterion donor describes a counterion donor comprising more than one charged functional group. Polyvalent counterion donors may be an entity covalently linked to more than one anionic functional group or an entity covalently linked to more than one cationic functional group.

All numbers herein may be understood as modified by "about." Unless otherwise specified, the term "about," when referring to a measurable value such as an amount, a temporal duration, and the like, is meant to encompass variations of ±10%, preferably ±5%, more preferably ±1%, and even more preferably ±0.1% from the specified value, as such variations are appropriate to modulate the percentage of the amphipathic therapeutic agent that remains encapsulated in the liposome. Unless otherwise specified, the term "about," when referring to a range, is meant to encompass variations of ±10% within the difference of the range, preferably ±5%, more preferably ±1%, and even more preferably ±0.1% from the specified value, as such variations are appropriate to reduce the side effects of steroids.

As used herein, the term "alkyl" refers to a straight or branched, saturated, aliphatic radical having from 1 to about 10 carbon atoms. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, and decyl.

As used herein, the term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be 15 monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 to 20 ring members, such as phenyl. "Substituted aryl" groups can be substituted with one or more groups selected from halo, hydroxy, amino, alkylamino, amido, acyl, nitro, cyano, and alkoxy.

"Pharmaceutically acceptable salts" of an amphipathic acid of the present invention are salts formed with bases, namely cationic salts such as alkali and alkaline earth metal salts, such as sodium, lithium, potassium, calcium, and magnesium, as well as ammonium salts, such as ammonium, trimethylammonium, diethylammonium, and tris-(hydroxymethyl)-methyl-ammonium salts.

Pharmaceutically acceptable salts of an amphipathic base of the present invention are salts formed with acids (e.g., acid addition salts) such as salts of mineral acids, organic carboxylic and organic sulfonic acids, e.g., hydrochloric acid, methanesulfonic acid, and maleic acid. Pharmaceutically acceptable salts of an amphipathic base of the present invention include citrate, sulfate, sulfonate, phosphate, pyrophosphate, tartrate, succinate, maleate, borate, carboxylate, glucoronate, chloride, hydroxide, nitrate, cyanate, or bromide salts.

The Liposome

The term "liposome" as used herein means multivesicular liposome (MVL), multilamellar vesicles (MLV), or small or large unilamellar vesicles (ULV). The liposomes are nano-sized and comprise a particle-forming component and an agent-carrying component. The particle-forming component forms an enclosed lipid barrier, and the agent carrying component comprises a medium enclosed by the particle-forming component.

The particle-forming component can be prepared from a phospholipid or a mixture of at least one phospholipid and cholesterol. Examples of the phospholipids used in the present invention include, but are not limited to, phosphatidylcholine (PC), phosphatidylglycerol (PG), phosphatidylethanolamine (PE), phosphatidylserine (PS), phosphatidic acid (PA), phosphatidylinositol (PI), egg phosphatidylcholine (EPC), egg phosphatidylglycerol (EPG), egg phosphatidylethanolamine (EPE), egg phosphatidylserine (EPS), egg phosphatidic acid (EPA), egg phosphatidylinositol (EPI), soy phosphatidylcholine (SPC), soy phosphatidylglycerol (SPG), soy phosphatidylethanolamine (SPE), soy phosphatidylserine (SPS), soy phosphatidic acid (SPA), soy phosphatidylinositol (SPI), dipalmitoylphosphatidylcholine (DPPC), 1,2-dioleoyl-sn-glycero-3-phosphatidylcholine (DOPC), dimyristoylphosphatidylcholine (DMPC), dipalmitoylphosphatidylglycerol (DPPG), dioleoylphosphatidylglycerol (DOPG), dimyristoylphosphatidylglycerol (DMPG), hexadecylphosphocholine (HEPC), hydrogenated soy phosphatidylcholine (HSPC), distearoylphosphatidylcholine (DSPC), distearoylphosphatidylglycerol (DSPG), dioleoylphosphatidylethanolamine (DOPE), palmitoyl-stearoylphosphatidylcholine (PSPC), palmitoyl-stearoylphosphatidylglycerol (PSPG), monooleoylphosphatidylethanolamine (MOPE), 1-palmitoyl-2-oleoyl-sn-glycero-3-phosphatidylcholine (POPC), distearoylphosphatidylethanolamine (DSPE), dipalmitoylphosphatidylserine (DPPS), 1,2-dioleoyl-sn-glycero-3-phosphatidylserine (DOPS), dimyristoylphosphatidylserine (DMPS), distearoylphosphatidylserine (DSPS), dipalmitoylphosphatidic acid (DPPA), 1,2-dioleoyl-sn-glycero-3-phosphatidic acid (DOPA), dimyristoylphosphatidic acid (DMPA), distearoylphosphatidic acid (DSPA), dipalmitoylphosphatidvlinositol (DPPI), 1,2-dioleoyl-sn-glycero-3-phosphatidylinositol (DOPI), dimyristoylphosphatidylinositol (DMPI), distearoylphosphatidylinositol (DSPI), and mixtures thereof.

In one embodiment, the particle-forming component includes a hydrophilic polymer with a long chain of highly hydrated flexible neutral polymer attached to a phospholipid molecule. Without being bound by any theory, the hydrophilic polymer is believed to stabilize the liposome and result in a longer circulation time in vivo. Examples of the hydrophilic polymer include, but are not limited to, polyethylene glycol (PEG) with a molecular weight of about 200 Daltons to about 5,000 Daltons, methoxy PEG (mPEG), ganglioside $GM_1$, polysialic acid, polylactic (also termed polylactide), polyglycolic acid (also termed polyglycolide), apolylacticpolyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose and synthetic polymers.

In one embodiment, the phospholipids are selected from DSPC and DSPE-PEG, wherein the molecular weight of PEG is about 2,000 Daltons (hereafter DSPE-$PEG_{2000}$).

In another embodiment, the molar ratio of DSPC, cholesterol and DSPE-$PEG_{2000}$ is about 3:2:0.45.

The particle-forming component may further comprise a lipid-conjugate of an antibody or a peptide that acts as a targeting moiety to enable the liposome to specifically bind to a target cell bearing a target molecule. Examples of the target molecules include, but are not limited to, epidermal growth factor receptor (EGFR), vascular endothelial growth factor receptor (VEGFR), carcinoembryonic antigen (CEA), and erbB-2/neu (HER2).

The liposomes have a mean particle diameter of about 30 nm to about 200 nm, or about 50 nm to about 150 nm.

The liposomes prepared in this invention can be generated by conventional techniques used to prepare vesicles. These techniques include, but not limited to, the ether injection method (Deamer et al., *Acad. Sci.* (1978) 308: 250), the surfactant method (Brunner et al., *Biochim. Biophys. Acta* (1976) 455: 322), the freeze-thaw method (Pick et al., *Arch. Biochim. Biophys.* (1981) 212: 186), the reverse-phase evaporation method (Szoka et al., *Biochim. Biophys. Acta.* (1980) 601: 559 71), the ultrasonic treatment method (Huang et al., *Biochemistry* (1969) 8: 344), the ethanol injection method (Kremer et al., *Biochemistry* (1977) 16: 3932), the extrusion method (Hope et al., *Biochim. Biophys. Acta* (1985) 812:55 65), the French press method (Barenholz et al., *FEBS Lett.* (1979) 99: 210) and methods detailed in Szoka, F., Jr., et al., *Ann. Rev. Biophys. Bioeng.* 9:467 (1980). All of the above processes are basic technologies for the formation of liposome vesicles and these processes are incorporated by reference herein.

The Therapeutic Agent

The therapeutic agent may be any appropriate therapeutic agent. In one embodiment, the therapeutic agent is an anti-cancer agent. Non-limiting examples of anti-cancer agents include vinca alkaloids, topoisomerase inhibitors, taxane compounds, derivatives thereof, and pharmaceutically acceptable salts thereof.

Examples of vinca alkaloids include, but are not limited to, vinorelbine, vincristine, vinblastine, and vindesine.

Examples of topoisomerase inhibitors include, but are not limited to, topotecan, camptothecin, irinotecan, etoposide, and doxorubicin.

Examples of taxane compounds include, but are not limited to, paclitaxel.

The Monovalent Counterion Donor

In one embodiment, the therapeutic agents are amphipathic bases with a net positive charge and the monovalent counterion donor within the liposome can be selected from an anionic ion or an entity which is covalently linked to an anionic functional group. The anionic ion or the anionic functional group of the monovalent counterion donor has a charge of −1, −2, or −3.

Non-limiting examples of monovalent counterion donors include, but are not limited to, benzenesulfonate and 4-hydroxybenzenesulfonate:

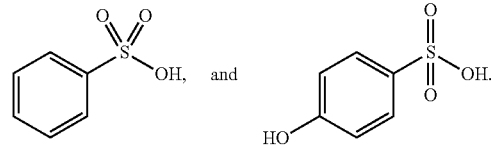 [SMILES: O=S(=O)(O)c1ccccc1 ; "and" ; O=S(=O)(O)c1ccc(O)cc1]

In another embodiment, the pharmaceutically acceptable salt of the monovalent counterion donor comprises a) an anionic ion or an entity which is covalently linked to an anionic functional group; and b) one or more cationic ions, wherein the anionic ion or the anionic functional group is ionically paired with the cationic ion(s).

The anionic ion or the anionic functional group can be selected from one or more of the following: citrate, sulfate, sulfonate, phosphate, pyrophosphate, tartrate, succinate, maleate, borate, carboxylate, glucoronate, chloride, hydroxide, nitrate, cyanate, or bromide. In one embodiment, the anionic ion and the anionic functional group is selected from the group consisting of citrate, sulfate, sulfonate, phosphate, pyrophosphate, carboxylate, and combinations thereof.

In yet another embodiment, the entity linked to the anionic functional group can be a natural or synthetic, organic, or inorganic compound. Examples of such entities include, but are not limited to, non-polymers (such as benzene, oligonucleotides, and monosaccharides), or polymers (such as polyvinyl), polyols (such as glycerol, sorbitol, and mannitol), polysaccharides, polypeptides, glycoproteins, and polynucleotides.

The cationic ion(s) of the pharmaceutically acceptable salt can be selected from one or more of the following: calcium ion, magnesium ion, sodium ion, potassium ion, manganese ion, or $NR_4^+$, wherein each R is independently H or an organic residue, and the organic residue is independently alkyl, alkylidene, heterocyclic alky, cycloalkyl, aryl, alkenyl, cycloalkenyl, or a hydroxyl-substituted derivative thereof, optionally including within its hydrocarbon chain a S, O, or N atom, forming an ether, ester, thioether, amine, or amide bond. In one embodiment, at least one cationic ion of the pharmaceutically acceptable salt is ammonium.

A second embodiment of the present invention provides for an amphipathic acidic therapeutic agent and a monovalent counterion donor within the liposome that may be selected from or include a cationic ion or an entity which is covalently linked to a cationic functional group. The cationic ion or the cationic functional group has a charge of +1, +2, or +3.

The pharmaceutically acceptable salt of the monovalent counterion donor comprises a) a cationic ion or an entity which is covalently linked to a cationic functional group; and b) one or more anionic ions, wherein the cationic ion or the cationic functional group is ionically paired with one or more anionic ions.

In one embodiment, the pharmaceutically acceptable salt of the monovalent counterion donor is ammonium sulfate. In one embodiment, the concentration of the monovalent counterion donor is about 100 mM to about 500 mM. In another embodiment, the concentration of the monovalent counterion donor is about 150 mM to about 450 mM. In yet another embodiment, the concentration of the monovalent counterion donor is about 200 mM to about 400 mM. In yet another embodiment, the concentration of the monovalent counterion donor is about 300 mM.

The Polyvalent Counterion Donor

In one embodiment, the therapeutic agent is an amphipathic base that forms a precipitate within the liposome with at least one polyvalent counterion donor.

In another embodiment, the polyvalent counterion donor includes an entity which is covalently linked with multiple anionic functional groups, wherein each anionic functional group has a charge of −1, −2, or −3. A pharmaceutically acceptable salt of an anionic polyvalent counterion donor comprises a) an entity covalently linked to multiple anionic functional groups; and b) one or more cationic ions, wherein the anionic functional group is ionically paired with at least one cationic ion.

Each anionic functional group of the polyvalent counterion is independently selected from the group consisting of: citrate, sulfate, sulfonate, phosphate, pyrophosphate, tartrate, succinate, maleate, borate, carboxylate, glucoronate, chloride, hydroxide, nitrate, cyanate, and bromide. In one embodiment, each anionic functional group is independently selected from the group consisting of: citrate, sulfate, sulfonate, phosphate, pyrophosphate, and carboxylate. For example, chondroitin sulfate is a polyvalent counterion donor with different anionic functional groups on the same entity, as illustrated below:

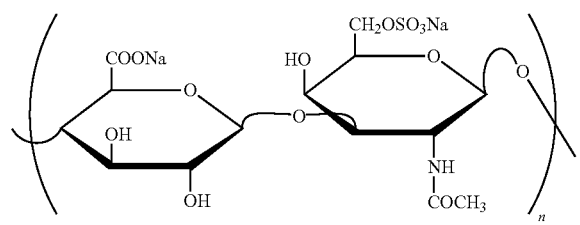

In some embodiments, at least one anionic functional group of the polyvalent counterion donor is sulfate.

The cationic ion is, for example, but is not limited to: calcium ion, magnesium ion, sodium ion, potassium ion, manganese ion, or $NR_4^+$, wherein each R is independently H or an organic residue and the organic residue is independently alkyl, alkylidene, heterocyclic alky, cycloalkyl, aryl, alkenyl, cycloalkenyl, or a hydroxyl-substituted derivative thereof, optionally including within its hydrocarbon chain a S, O, or N atom, forming an ether, ester, thioether, amine or amide bond. In one embodiment, at least one cationic ion is ammonium.

Another embodiment of the invention provides for an amphipathic acidic therapeutic agent, and a polyvalent counterion donor within the liposome that includes an entity which is covalently linked to multiple cationic functional groups and each cationic group has a charge of +1, +2, or +3. The amphipathic acid forms an insoluble salt with the polyvalent counterion donor and is trapped inside the liposome.

The pharmaceutically acceptable salt of the cationic polyvalent counterion donor comprises a) an entity which is covalently linked to one or more cationic functional groups; and b) one or more anionic ions, wherein the cationic functional group is ionically paired with at least one anionic ion.

The entity of the polyvalent counterion donor can be a natural or synthetic, organic or inorganic compound. Non-limiting examples of the entity include non-polymers such as oligonucleotides and monosaccharides, or polymers (such as polyvinyls), polyols (such as glycerol, sorbitol and mannitol), polysaccharides (such as dextran and chitosan), polypeptides, glycoproteins, and polynucleotides.

In one embodiment, the polyvalent counterion donor is selected from one or more of the following: sulfated heparin, carrageenan, mucin, sulfated hyaluronic acid, chondroitin sulfate, keratin sulfate, dermatan sulfate or sulfated polysaccharide. Non-limiting examples of sulfated polysaccharides include dextran sulfate, with a molecular weight of about 1,000 Daltons to about 20,000 Daltons, or with a molecular weight of about 1,600 Daltons to about 8,000 Daltons.

In one embodiment, the pharmaceutically acceptable salt of dextran sulfate is selected from ammonium dextran sulfate and sodium dextran sulfate.

The Pharmaceutical Composition

Liposomal anti-cancer treatments comprising a monovalent counterion donor but not a polyvalent counterion donor present a low encapsulation efficiency and/or retention profile, whereas liposomal anti-cancer-treatments comprising a polyvalent counterion donor but not a monovalent counterion donor present higher encapsulation efficiency and/or retention profile. However, liposomal formulations comprising a polyvalent but not monovalent counterion donor are also associated with high toxicity, including skin toxicity. The present invention is based in part on the inventor's discovery that combining a polyvalent counterion donor or a pharmaceutically acceptable salt thereof with a monovalent counterion donor or a pharmaceutically acceptable salt thereof preserves therapeutic efficiency, while also minimizing toxicity. As such, the pharmaceutical compositions of the present invention address the unmet need for effective liposomal anti-cancer treatments that cause less severe side effects, such as but not limited to skin toxicity.

In one embodiment, the pharmaceutical composition of the present invention comprises a) at least one liposome having a particle-forming component selected from a phospholipid or a mixture of at least one phospholipid and cholesterol, b) at least one polyvalent counterion donor or a pharmaceutically acceptable salt thereof; c) at least one monovalent counterion donor or a pharmaceutically acceptable salt thereof; and d) an amphipathic therapeutic agent, a derivative thereof, or a pharmaceutically acceptable salt thereof.

In another embodiment, the pharmaceutical composition of the present invention comprises a) at least one liposome having a particle-forming component selected from a mixture of one or more phospholipids and cholesterol, b) at least one polyvalent counterion donor or a pharmaceutically acceptable salt thereof with a concentration between about 0.1 mM to about 10 mM; c) at least one monovalent counterion donor or a pharmaceutically acceptable salt thereof with a concentration of about 150 mM to about 450 mM; and d) a vinca alkaloid. In yet another embodiment, the particle-forming component further comprises a hydrophilic polymer.

In some embodiments, the pharmaceutical composition of the present invention further comprises a compound for liposome loading, such as an ammonium compound. In one embodiment, the ammonium compound for liposome loading is selected from the group of ammonium, trimethylammonium, diethylammonium, and tris-(hydroxymethyl)-methyl-ammonium salts. In one embodiment, the ammonium compound for liposome loading is $NR_4^+$, wherein each R is independently H or an organic residue, and the organic residue is independently alkyl, alkylidene, heterocyclic alky, cycloalkyl, aryl, alkenyl, cycloalkenyl, or a hydroxyl-substituted derivative thereof, optionally including within its hydrocarbon chain a S, O, or N atom, forming an ether, ester, thioether, amine, or amide bond. In one embodiment the ammonium compound is ammonium sulfosalicylate.

The valency of each polyvalent counterion donor is determined by the average number of cationic functional groups (for a cationic polyvalent counterion donor) or anionic functional groups (for an anionic polyvalent counterion donor) covalently linked to the corresponding entity of the polyvalent counterion donor.

In an illustrative example, the polyvalent counterion donor is dextran sulfate. The entity being dextran comprises a heterogeneous population wherein an individual dextran has a molecular weight between 1,000 Daltons and 20,000 Daltons and is covalently linked to multiple sulfonate groups. The valency, the average number of the multiple sulfonate groups covalently linked to the corresponding entity of the polyvalent counterion donor, ranges from 7.5 to 8.0. In another illustrative example, the polyvalent counterion donor is sulfated heparin. The entity being heparin comprises a heterogenous population wherein an individual heparin has a molecular weight between 1,600 to 8,000 Daltons and is covalently linked to multiple sulfonate groups. The valency of such a polyvalent counterion donor ranges from 2 to 50; 2 to 40; or 2 to 24. In one embodiment, the valency of dextran sulfate ranges from 6.5 to 7.9. In another embodiment, the valency of the polyvalent counterion donor being sucroseoctasulfate is 8.

The total valency per volume of the polyvalent counterion donor is determined by multiplying the number (mole, mmole etc.) of the polyvalent counterion donor per volume by the valency of the same.

In one group of embodiments, the anionic functional groups of the polyvalent counterion donor or its pharmaceutically acceptable salt have a total valency per volume, e.g., the equivalence for counteracting with the therapeutic agent, of about 1 milliequivalent per liter (mEq/L) to about 160 mEq/L, about 3 mEq/L to about 160 mEq/L, about 1 mEq/L to about 320 mEq/L, about 1 mEq/L to about 250 mEq/L, about 3 mEq/L to about 250 mEq/L, about 160 mEq/L to about 250 mEq/L, or about 160 mEq/L to about 320 mEq/L.

In other embodiments, the concentration of the polyvalent counterion donor or its pharmaceutically acceptable salt is about 2 mM to less than 8 mM, about 0.1 mM to less than 8 mM, about 0.1 mM to about 10 mM, about 2 mM to less than 10 mM, or any value or range between 0.1 mM to 10 mM.

The pharmaceutical composition is formulated for any suitable route of administration including intracranial, intracerebral, intraventricular, intrathecal, intraspinal, oral, topical, rectal, transdermal, subcutaneous, intravenous, intramuscular intranasal, intraperitoneal, intratumor, and the like.

The dosage of the pharmaceutical composition of the present invention can be determined by one skilled in the art according to the embodiments. Unit doses or multiple dose forms are contemplated, each offering advantages in certain clinical settings. According to the present invention, the actual amount of the pharmaceutical composition to be administered can vary in accordance with the age, weight, and/or general condition of the subject to be treated, the type of cancer, the toxicity of the composition, and/or the discretion of medical professionals.

In some embodiments, at least a portion of the therapeutic agent (such as vinorelbine) forms a salt with the polyvalent counterion donor and precipitates in the intraliposomal aqueous core, as evident in FIG. 1.

The Method of Inhibiting Cancer Cell Growth

The invention is directed to methods of inhibiting cancer cell growth in a subject, which comprises administering an effective amount of the pharmaceutical composition described herein to a subject in need thereof, whereby the symptoms and signs of the cancer and/or toxicity in the subject are reduced.

The pharmaceutical composition may be administered alone, or as an adjuvant to surgery, e.g., before surgery to reduce the tumor size and/or following surgery to reduce the possibility of metastases, e.g., by inhibiting the growth and migration of circulating tumor cells through the blood stream.

The pharmaceutical composition can be administered before, after, or simultaneously with one or more other anti-cancer agents. Other anti-cancer agents include conventional chemotherapeutic agents, target cancer therapies, or radiation therapy.

Conventional chemotherapeutic agents comprise DNA synthesis inhibitors, alkylating agents, antifolate agents, metabolic inhibitors, or combinations thereof.

Target cancer therapies are medications that inhibit the growth of cancer cells by interfering with specific targeted molecules needed for carcinogenesis and cancer growth, rather than by simply interfering with rapidly dividing cells (e.g., with a conventional chemotherapeutic agent). Target cancer therapies comprise kinase inhibitors, angiogenesis inhibitors, epidermal growth factor receptor (EGFR) inhibitors, HER2/neu receptors or combinations thereof.

Radiation therapy uses high-energy radiation to shrink tumors and kill cancer cells. Examples of radiation therapy include X-rays, gamma rays, and charged particles.

The following examples further illustrate the present invention. These examples are intended merely to be illustrative of the present invention and are not to be construed as being limiting.

Example 1: Preparation of Liposomes

The liposomes were prepared by the solvent injection method. The lipids, including DSPC, DSPE-PEG$_{2000}$ and cholesterol, were combined at a molar ratio of 3:0.045:2 and dissolved in 99.9% ethanol at about 60° C. in a flask. A tabletop ultrasonic bath was used for lipid dissolution.

The dissolved lipid solution was added to a 1.0 mM sodium phosphate solution or an indicated solution with a counterion donor at 100 mL/min by a peristaltic pump and the two solutions were mixed. The lipid mixture was then passed 6-10 times through a polycarbonate membrane with a pore size of 0.2 μm and then passed 6-10 times through a polycarbonate membrane with a pore size of 0.1 μm. Liposomes (or large multilamellar vesicles) were formed and the average vesicle diameter was about 100-120 nm (measured using a Malvern ZetaSizer Nano ZS-90).

The liposome mixture was dialyzed and concentrated by tangential flow filtration against a 0.9% (w/w) sodium chloride and 9% (w/w) sucrose solution with a Millipore Pellicon 2 Mini Ultrafiltration Module Biomax-100C (0.1 m$^2$), and then sterilized using a 0.2 μm sterile filter.

Example 2: Effect of Monovalent Counterion Donor on the Encapsulation Efficiency and Retention Profile The liposome was prepared by the process in Example 1 with ammonium sulfate. A gradient across the lipid bilayer membrane of the liposome was established using 300 mM and 600 mM of ammonium sulfate, for remote loading of vinorelbine. The encapsulating (loading) efficiency and the retention profile of liposomal vinorelbine were assessed. The prepared liposomal vinorelbine was subject to an in vitro release assay at a ratio of the analyte to human plasma of 1 to 99 by volume and then incubated at 37° C. for a designated time interval. The vinorelbine in the sample was further separated into free vinorelbine and liposomal vinorelbine by size exclusion chromatography. The percentage of encapsulated vinorelbine remaining after plasma incubation was calculated by dividing the measured amount of the liposomal vinorelbine of the sample obtained after plasma incubation by that of the initial sample, and the results are summarized in Table 1.

Results: The data shows ammonium sulfate was effective in loading or encapsulating vinorelbine in the liposome. However, ammonium sulfate was less effective in retaining vinorelbine in the liposome, with less than 30% of vinorelbine remaining encapsulated in the liposome after 24 hours of plasma incubation.

TABLE 1

Characteristics of pharmaceutical compositions having monovalent counterion donors

| Pharmaceutical Composition | Concentration of Monovalent Counterion Donor | Particle size [nm] | Encapsulation Efficiency [%] | % of encapsulated vinorelbine remaining after 24 h plasma incubation |
|---|---|---|---|---|
| LV001 | 300 mM ammonium sulfate | 93.3 | 93 | 28.7 |
| LV006 | 600 mM ammonium sulfate | 93.6 | 93 | 24.7 |

Example 3: Effect of Polyvalent Counterion Donor on the Encapsulation Efficiency and Retention Profile Sodium dextran sulfate with a molecular weight of 8.000 Daltons was converted to ammonium dextran sulfate (a pharmaceutically acceptable salt of dextran sulfate) using a DOWEX ion exchange column. Two pharmaceutical compositions were prepared by the method in Example 1 with 4 mM and 8 mM ammonium dextran sulfate, respectively, followed by the remote loading of about 2 mg of vinorelbine, incubated at about 60° C.

The encapsulating efficiency and the retention profile of liposomal vinorelbine in these two pharmaceutical compositions were assessed. The retention profile of liposomal vinorelbine was subject to an in vitro plasma release method and the results are summarized in Table 2.

Results: 8 mM ammonium dextran sulfate resulted in an encapsulation efficiency of 93%, whereas the encapsulating efficiency for 4 mM ammonium dextran sulfate was below 90%. Similarly, the LV009 formulation in Table 4 included polyvalent counterion donor only and had less than 90% encapsulation efficiency and a retention rate of 98.74% after 24 hours plasma incubation.

TABLE 2

Characteristics of pharmaceutical compositions having polyvalent counterion donors.

| Pharmaceutical Composition | Polyvalent Counterion Donor Salt Ammonium dextran sulfate (MW = 8,000 Daltons) | Particle size (nm) | Encapsulating Efficiency (%) |
|---|---|---|---|
| LV702 | 4 mM | 114 | 84 |
| LV703 | 8 mM | 114 | 93 |

Example 4: Effect of Combination of Mono- and Polyvalent Counterion Donors

An in vitro study was conducted to assess the effects of combinations of mono- and polyvalent counterion donors on the retention profile of liposomal vinorelbine.

Liposomes were prepared according to Example 1 with 300 mM ammonium sulfate and various concentrations of sodium dextran sulfate.

The encapsulating efficiency and the retention profile of various liposomal vinorelbines were assessed. The retention profile of various liposomal vinorelbines was obtained by using the 24-hour in vitro plasma release method and the results are summarized in Table 3.

Results: The data demonstrate that the various combinations of mono- and polyvalent counterion donors maintain the encapsulation efficiency of vinorelbine, and the liposome size was around 100 nm. In addition, the retention profile of liposomal vinorelbine depends on the concentration of the polyvalent counterion donor. 8 mM sodium dextran sulfate was associated with a higher percentage of vinorelbine retention at 24 hours (78.9%) than that of 2 mM sodium dextran sulfate (51.8%).

TABLE 3

Characteristics of liposomal vinorelbine with mono- and polyvalent counterion donor combination

| Pharmaceutical Composition | Counterion donor concentration (mM) | | Particle size (nm) | Encapsulation Efficiency (%) | % of encapsulated vinorelbine remaining after 24 h plasma incubation |
| --- | --- | --- | --- | --- | --- |
| | Ammonium Sulfate | Sodium Dextran Sulfate | | | |
| LV301 | 300 | 2 | 106.2 | 101.6 | 51.8 |
| LV302 | 300 | 4 | 104.5 | 106.3 | 67.3 |
| LV303 | 300 | 8 | 101.5 | 104.6 | 78.9 |

Example 5: Effect of Various Polyvalent Counterion Donor Salts

An in vitro study was conducted to assess the effect of different polyvalent counterion donor salts on the retention profile of liposomal vinorelbine.

Liposomes prepared according to Example 1 were mixed with 300 mM ammonium sulfate (AS) and two different polyvalent counterion donor salts: dextran sulfate (DS) sodium salt and DS ammonium salt.

The encapsulating efficiency and the retention profile of liposomal vinorelbine were assessed. The retention profile of liposomal vinorelbine was obtained by using the 24-hour in vitro plasma release method and the results are summarized in Table 4.

Results: The data shows that the DS sodium salt and DS ammonium salt were equally effective in retaining vinorelbine in the liposome after 24 hours of plasma incubation. In addition, when the concentration of polyvalent counterion donor or its salt was 10 mM, the retention profile of the mono- and polyvalent counterion donor combination (100% and 94.2% of vinorelbine remaining in the liposome at 24 hours) was similar to that of the polyvalent counterion donor composition (98.7% of vinorelbine remaining in the liposome after 24 hours). This is in contrast with the data in Table 3, wherein when the concentration of the polyvalent counterion donor was less than 10 mM, the retention profile of liposomal vinorelbine depends on the concentration of the polyvalent counterion donor.

TABLE 4

Characteristics of liposomal vinorelbine with mono- and polyvalent counterion donor combination

| Pharmaceutical Composition | Counterion Donor Combination | Particle size (nm) | Encapsulation Efficiency | % of encapsulated vinorelbine remaining after 24 h plasma incubation |
| --- | --- | --- | --- | --- |
| LV007 | 300 mM AS 10 mM DS sodium salt | 112.7 | 85.1% | 100 |

TABLE 4-continued

Characteristics of liposomal vinorelbine with mono- and polyvalent counterion donor combination

| Pharmaceutical Composition | Counterion Donor Combination | Particle size (nm) | Encapsulation Efficiency | % of encapsulated vinorelbine remaining after 24 h plasma incubation |
|---|---|---|---|---|
| LV008 | 300 mM AS 10 mM DS ammonium salt | 114.1 | 83.7% | 94.2 |
| LV009 | 10 mM DS ammonium salt | 108.8 | 89.4% | 98.7 |

Example 6: Effect of Various Molecular Weight Polyvalent Counterion Donors

The effect of the molecular weight of the polyvalent counterion donor on the liposomal vinorelbine retention profile was assessed. Liposomes prepared according to Example 1 were mixed with ammonium sulfate and 5,000 Dalton or 8,000 Dalton dextran sulfate.

The encapsulating efficiency and the retention profile of liposomal vinorelbine were assessed. The retention profile of liposomal vinorelbine was obtained by using the 24-hour in vitro plasma release method and the results are summarized in Table 5.

Results: The total valency per volume of the polyvalent counterion donor affects the retention profile of liposomal vinorelbine. The data indicates that a polyvalent counterion donor with higher valency is associated with more encapsulated vinorelbine at 24 hours.

ammonium sulfate and various concentrations of dextran sulfate, followed by the remote loading of vinorelbine. The encapsulation efficiency and the retention profile of liposomal vinorelbine were assessed. The retention profile of liposomal vinorelbine was obtained by using the 24-hour in vitro plasma release method and are summarized in Tables 6 to 8.

Results of Table 6: At 72 hours, 72.2% of encapsulated vinorelbine remained in the NanoVNB® composition (a pharmaceutical composition comprising the polyvalent counterion donor triethylamine sucrose octasulfate, but no monovalent counterion donor) and this high retention rate at 72 hours can lead to toxicity, most notably skin toxicity. On the other hand, all of the encapsulated vinorelbine was released from the LV005 composition (a pharmaceutical composition comprising only a monovalent counterion donor) at 72 hours, and such poor retention is associated

TABLE 5

Characteristics of liposomal vinorelbine with various molecular weights of polyvalent counterion donor.

| Pharmaceutical Composition | Ammonium Sulfate Concentration (mM) | Dextran Sulfate Concentration (mM)/molecular weight in kiloDaltons (kDa) | Particle size (nm) | Total valency per volume (mEq/L) | % of encapsulated vinorelbine remaining after 24 h plasma incubation |
|---|---|---|---|---|---|
| LV108 | 300 | 3 mM/5 kDa | 110.0 | 73.68 | 55.9 |
| LV102 | 300 | 6 mM/5 kDa | 114.5 | 147.36 | 67.7 |
| LV301 | 300 | 2 mM/8 kDa | 106.2 | 78.64 | 51.8 |
| LV302 | 300 | 4 mM/8 kDa | 104.5 | 157.28 | 67.3 |

Example 7: Adjustable Retention Profile Using Mono- and Polyvalent Counterion Donor Combinations Various pharmaceutical compositions were prepared by the process in Example 1 with various concentrations of with low therapeutic efficacy. By combining mono- and polyvalent counterion donors, a range of liposomal vinorelbine retention profiles was obtained. It is noted that the total valency per volume of the polyvalent counterion donor or its pharmaceutically acceptable salt is about 1 mEq/L to about 240 mEq/L inside the liposome.

TABLE 6

Characteristics of pharmaceutical compositions with 100 mM and 300 mM monovalent counterion donor and various concentrations of polyvalent counterion donor

| Pharmaceutical Composition | Dextran Sulfate MW (kDa) | Dextran Sulfate Concentration (mM) | Total valency per volume mEq/L | [Ammonium sulfate] mM | % of encapsulated vinorelbine remaining At 24 h | % of encapsulated vinorelbine remaining At 72 h |
|---|---|---|---|---|---|---|
| LV005 | — | — | | 300 | 19.8 | N.D. |
| LV305 | 8 | 0.3 | 11.79 | 300 | 44.1 | 27.1 |

TABLE 6-continued

Characteristics of pharmaceutical compositions with 100 mM and 300 mM monovalent counterion donor and various concentrations of polyvalent counterion donor

| Pharmaceutical Composition | Dextran Sulfate MW (kDa) | Dextran Sulfate Concentration (mM) | Total valency per volume mEq/L | [Ammonium sulfate] mM | % of encapsulated vinorelbine remaining At 24 h | % of encapsulated vinorelbine remaining At 72 h |
|---|---|---|---|---|---|---|
| LV306 | | 0.6 | 23.59 | | Not tested | 31.6 |
| LV301 | | 2 | 78.62 | | 59.2 | 44.4 |
| LV304 | | 3 | 117.93 | | 65.1 | Not tested |
| LV302 | | 4 | 157.24 | | 77.1 | 58.6 |
| LV303 | | 8 | 314.48 | | 90.1 | Not tested |
| LV402 | 1.6 | 0.25 | 1.97 | | 47.4 | 16.5 |
| LV403 | | 0.5 | 3.93 | | 53.5 | 20.7 |
| LV404 | | 1 | 7.86 | | 53.3 | 24.3 |
| LV401 | | 1.5 | 11.79 | | 39 | 20 |
| NanoVNB ® | 1.2 | 75 mM triethylamine sucrose octasulfate | 600 | None | 82.2 | 72.2 |
| LV307 | 8 | 6 | 235.86 | 300 | 49.1 | 19.6 |
| LV801 | 8 | 4 | 157.2 | 100 | 55.8 | 15.3 |

TABLE 7

Characteristics of the pharmaceutical compositions with various concentrations of monovalent counterion donor and a fixed concentration (0.3 mM) of polyvalent counterion donor

| Pharmaceutical Composition | Ammonium Sulfate (mM) | Sodium Dextran Sulfate (mM) | Particle size (nm) | Encapsulation Efficiency (%) |
|---|---|---|---|---|
| LV801 | 50 | 0.3 | 102.3 | 44.4 |
| LV802 | 100 | 0.3 | 101.2 | 72.4 |
| LV803 | 200 | 0.3 | 106.9 | 102.8 |
| LV305 | 300 | 0.3 | 122.1 | 102.6 |
| LV804 | 400 | 0.3 | 106.1 | 87.9 |
| LV805 | 500 | 0.3 | 111.2 | 70.4 |
| LV806 | 600 | 0.3 | 106.5 | 48.3 |

Results of Table 7: the encapsulation efficiency of vinorelbine was above 70% using 100 mM to 500 mM of ammonium sulfate.

TABLE 8

Characteristics of the pharmaceutical compositions with various concentrations of monovalent counterion donor and a fixed concentration (0.3 mM) of polyvalent counterion donor

| Pharmaceutical Composition | Ammonium Sulfate (mM) | Sodium Dextran Sulfate (mM) | Particle size (nm) | Encapsulation Efficiency (%) | % of encapsulated vinorelbine remaining after 24 h plasma incubation |
|---|---|---|---|---|---|
| NanoVNB ® | — | — | 97.2 | 100.9 | 80.3 |
| LV803 | 200 | 0.3 | 106.9 | 102.8 | 32.0 |
| LV305 | 300 | 0.3 | 122.1 | 102.6 | 44.1 |
| LV804 | 400 | 0.3 | 106.1 | 87.9 | 37.4 |

Results of Table 8: more than 30% of liposomal vinorelbine was retained after 24-hour of incubation using 200-400 mM of ammonium sulfate (monovalent counterion donor).

Example 8: In Vivo Anti-Cancer Evaluation Using HT-29 Human Colon Cancer Cells

An in vivo anti-cancer evaluation of the LV304 pharmaceutical composition was performed using an orthotopic HT-29 human colon tumor model in mice.

Mice had free access to drinking water and food at all time during this trial.

The study design involved 3 study groups as follows:

NanoNVB® Group: 6 mice were given 25 mg/kg of vinorelbine as NanoVNB®, once daily by intravenous injection on days 0, 3, 6 and 9.

LV304 Group: 6 mice were given 25 mg/kg of vinorelbine as LV304 pharmaceutical composition, once daily by intravenous injection on days 0, 3, 6 and 9.

Control Group: 6 mice were given a once daily intravenous saline injection on days 0, 3, 6 and 9.

During the study period, the following outcomes were measured:

Percentage of tumor growth change (% T/C). This was calculated by the following formula:

$$(\text{Tumor weight}_{day\ x} - \text{Tumor weight}_{day\ 0})_{treated} / (\text{Tumor weight}_{day\ x} - \text{Tumor weight}_{day\ 0})_{control} \times 100\%.$$

Maximum body weight change, compare to the body weight on Day 0.

Mean tumor doubling time (TDT). This is widely used for quantification of tumor growth rate and is calculated by the following formula:

$$(\text{day x} - \text{day 0})$$

day x was the time taken for the tumor volume to double compared with the starting size.

Skin Toxicity Score, assessed and graded based on the parameters listed in Table 9.

TABLE 9

Skin Toxicity Score

| | Signs & Severity | |
| --- | --- | --- |
| Grade | Hair loss & edema around the eyelid | Hair loss around the groin |
| 0 | None | None |
| 1 | Slight | Slight |
| 2 | Moderate | Moderate |
| 3 | Severe | Severe |
| 4 | Very severe | Very severe |

Result:

Table 10 shows the percentage of tumor growth change (% T/C) on day 8 was similar between the NanoVNB® and LV304 groups (−41.0% for NanoVNB® and −42.4% LV304). The mean tumor doubling time (Mean TDT) was >78 days in the NanoVNB® group, 67.1 days in LV304 group and 7.6 days in the control group. In addition, mice receiving LV304 displayed fewer side effects (less weight loss and lower skin toxicity score) relative to mice receiving NanoVNB®.

Figure 2:
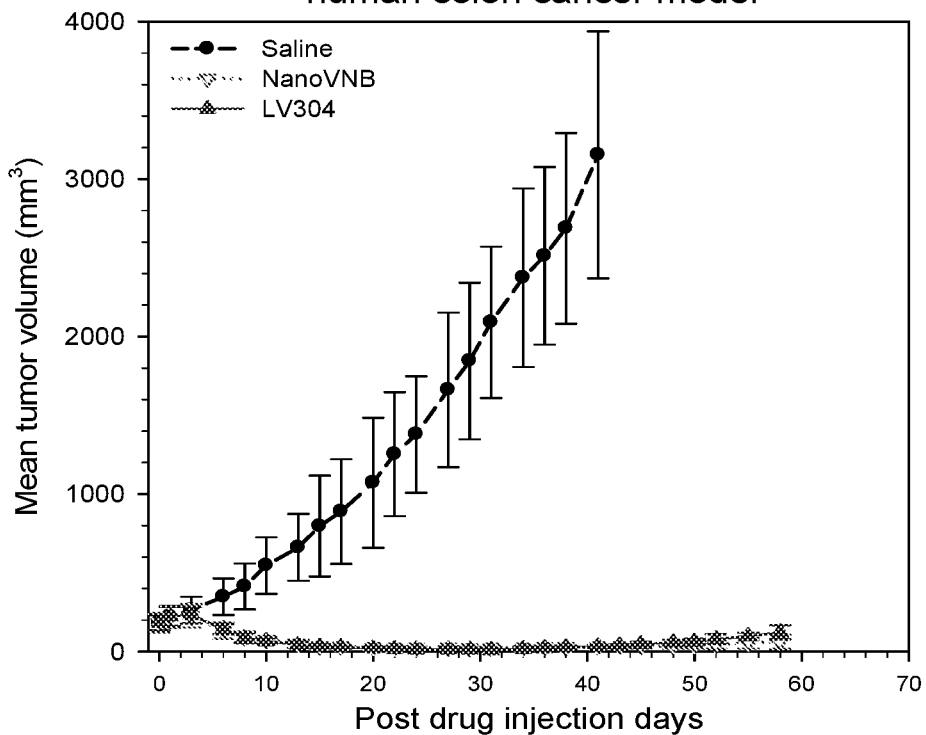
FIG. 2 shows the mean tumor volume in the NanoVNB® group, the LV304 group and the saline (control) group.

FIG. 2 shows the mean tumor volume in the NanoVNB® group, the LV304 group and the saline (control) group. The results indicate that the mean tumor volume in the NanoVNB® and LV304 groups were lower than 200 mm³ throughout the study period, whereas the mean tumor volume in the control group exceeded 3000 mm³ at day 40.

These results indicate that LV304 is an effective anti-cancer therapeutic agent relative to NanoVNB®, and caused less severe side effects than did NanoVNB®.

TABLE 10

Anti-cancer evaluation of NanoVNB ®, LV304 and saline in HT-29 human colon cancer model

| Treatment Group | % T/C (day)* | Max. % BW change (day)* | Skin Toxicity Score (day)* | Mean TDT |
| --- | --- | --- | --- | --- |
| Saline | — | −10.3 (34) | — | 7.0 ± 2.4 |
| NanoVNB ® | −41.0 ± 15.4 (8) | −20.8 (13) | 37 (17) | >78 |
| LV304 | −42.4 ± 13.1 (8) | −4.7 (13) | 20 (15) | 67.1 ± 5.4 |

*number of days after Day 0

Example 9: In Vivo Anti-Cancer Evaluation Using PC14PE6/AS2 Human Lung Adenocarcinoma Orthotopic Model An in vivo anti-cancer evaluation of the LV304 pharmaceutical composition was performed using an orthotopic PC14PE6/AS2 lung tumor model in mice.

The study design involved 3 study groups as follows:

NanoVNB® Group: 6 mice were given 50% of the maximum tolerated dose (MTD) of NanoVNB® (½ MTD=7.5 mg/kg of vinorelbine) as a single intravenous injection on day 0.

LV304 Group: 6 mice were given 50% of the MTD of LV304 pharmaceutical composition (½ MTD=10 mg/kg of vinorelbine) as a single intravenous injection on day 0.

Control Group: 6 mice were given a single saline intravenous injection on day 0.

During the study period, the following outcomes were measured:

Maximum body weight change, compare to the body weight on Day 0.

Mean survival time.

Figure 3:
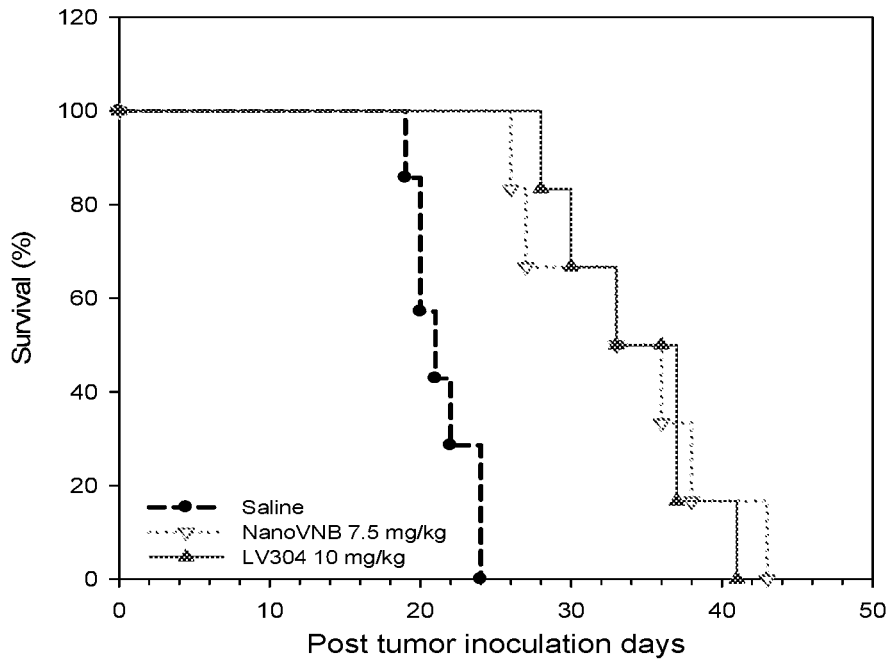
FIG. 3 shows the mean survival time in the NanoVNB® group, the LV304 group and the saline (control) group.

Results: Referring to Table 11, the mean survival time for mice was 33.8 days after a single NanoVNB® injection, 34.2 days after a single LV304 injection and 21.4 days after a single saline injection. FIG. 3 shows that the survival times in the NanoVNB® group and the LV304 group were significant longer compared to that in the saline (control) group (p<0.01).

TABLE 11

Anti-cancer evaluation of NanoVNB ®, LV304, and saline groups in PC14PE6/AS2 human lung adenocarcinoma orthotopic model.

| Treatment Group | Max. % BW change (day)* | Mean survival time ± SD (days) |
| --- | --- | --- |
| Saline | −3.6 (18) | 21.4 ± 2.0 |
| NanoVNB ® | −12.6 (9) | 33.8 ± 6.6 |
| LV304 | −17.0 (9) | 34.2 ± 4.8 |

*days after drug administration on Day 0

Example 10: In Vivo Skin Toxicity Evaluation Using SCID Mouse Model

An in vivo skin toxicity evaluation of the LV304 pharmaceutical composition was performed using BALB/c mice. Mice had free access to drinking water and food at all time during this trial and were randomized into 3 study groups as follows:

NanoVNB® Group: 6 mice received vinorelbine in the form of NanoVNB®, through a daily IV injection on day 0 (7.5 mg/kg), day 3 (5 mg/kg), day 6 (5 mg/kg), and day 9 (7.5 mg/kg).

LV304 Group: 6 mice received vinorelbine in the form of LV304, through a daily IV injection on day 0 (7.5 mg/kg), day 3 (5 mg/kg), day 6 (5 mg/kg), and day 9 (7.5 mg/kg).

Control Group: 6 mice received a once daily IV saline injection on days 0, 3, 6 and 9.

During the study period, skin toxicity was assessed and scored based on the grading system in Table 9.

Figure 4:
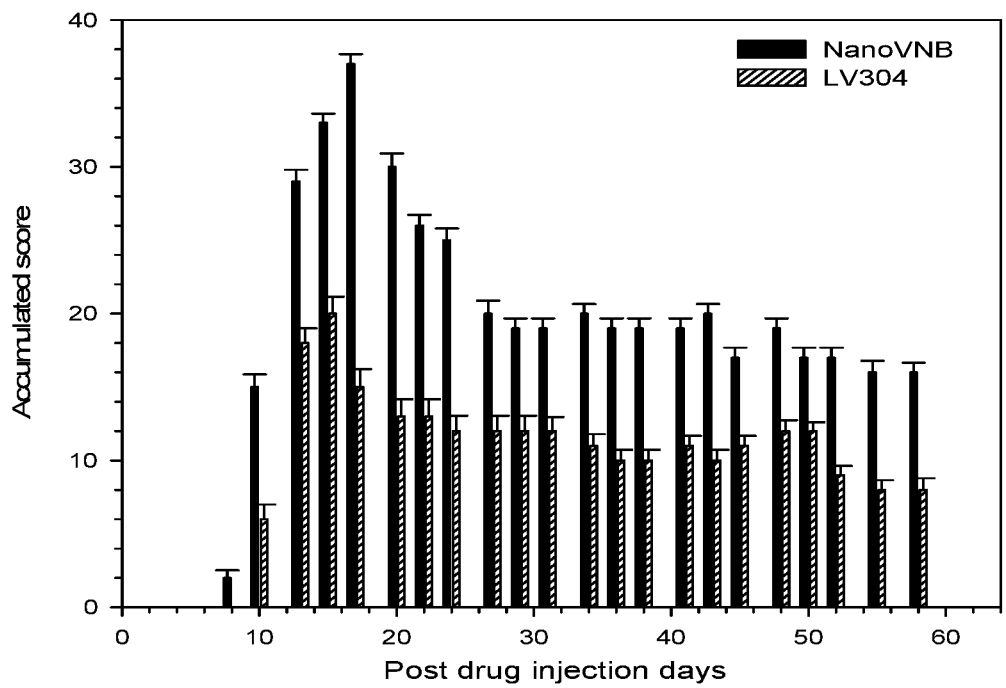
FIG. 4 shows the skin toxicity score in the NanoVNB® group and the LV304 group.

Results: FIG. 4 shows the skin toxicity scores in the NanoVNB® group and the LV304 group. The skin toxicity in the LV304 group was significantly lower compared to the NanoVNB® group throughout the 60-day trial period.

Figure 5:
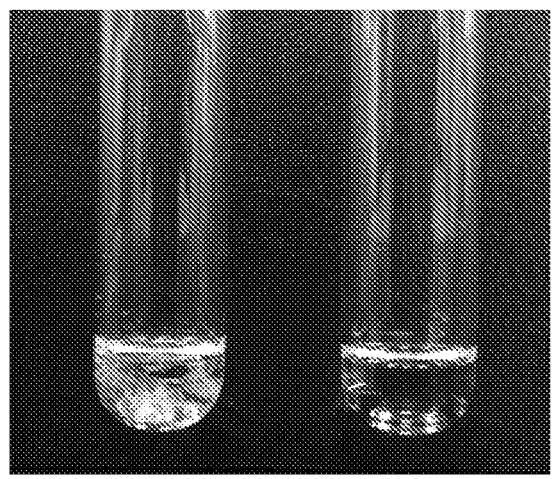
FIG. 5 shows precipitation of sodium dextran sulfate and vinorelbine (left); and no visible precipitation of ammonium sulfate and vinorelbine (right)
Figure 6:
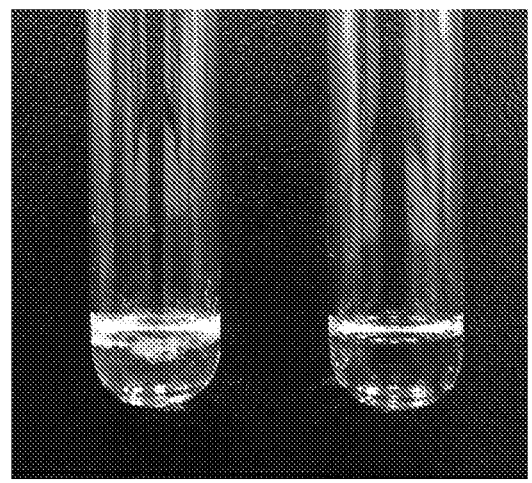
FIG. 6 shows precipitation of sodium dextran sulfate and irinotecan (left); and no visible precipitation of ammonium sulfate and irinotecan (right)

Example 11: Adjustable Retention Profile Assayed by Precipitation Effect of Vinorelbine with Mono- and Polyvalent Counterion Donor Combinations As shown in Example 7, the percentage of encapsulated vinorelbine remaining after plasma incubation is adjustable according to the present invention. The percentage of encapsulated therapeutic agent remaining after plasma incubation can be monitored by precipitation among encapsulated therapeutic agent(s) and counterion donor(s) in the aqueous environment as in FIG. 1, FIG. 5, and FIG. 6. The counterion donors could be selected from monovalent counterion donor(s), polyvalent counterion donor(s), or a combination thereof. The interaction among encapsulated therapeutic agent(s), monovalent counterion donor(s), and polyvalent counterion donor(s) results in insoluble precipitate in the aqueous environment, with the extent of precipitation demonstrating the ability of how much the encapsulated therapeutic agent can be released and mimicking the adjustable retention profile of the corresponding therapeutic agent.

To examine the precipitation, therapeutic agent solution(s) and counterion donor(s), or therapeutic agent solution(s) and combination of counterion donors were mixed, followed by vigorous agitation and high speed centrifugation to separate insoluble precipitate and free form therapeutic agent(s). The concentration of the free form therapeutic agent(s) was determined by measuring the corresponding absorbance with a plate reader.

Various compositions were prepared by mixing 60 mg/mL of vinorelbine solution and liposomes with 1 mM to 22.5 mM of dextran sulfate (molecular weight 1,600), or with 300 mM of ammonium sulfate and 1 mM to 22.5 mM of dextran sulfate (molecular weight 1,600), followed by vigorous agitation by vortex and centrifugation at 21,460×g for 30 minutes to separate insoluble precipitate from free-form vinorelbine. The volume ratio for mixing the vinorelbine solution and the counterion donor solution was 1:2, with the final equivalent counterion donor concentrations shown in Table 12.

Figure 7:
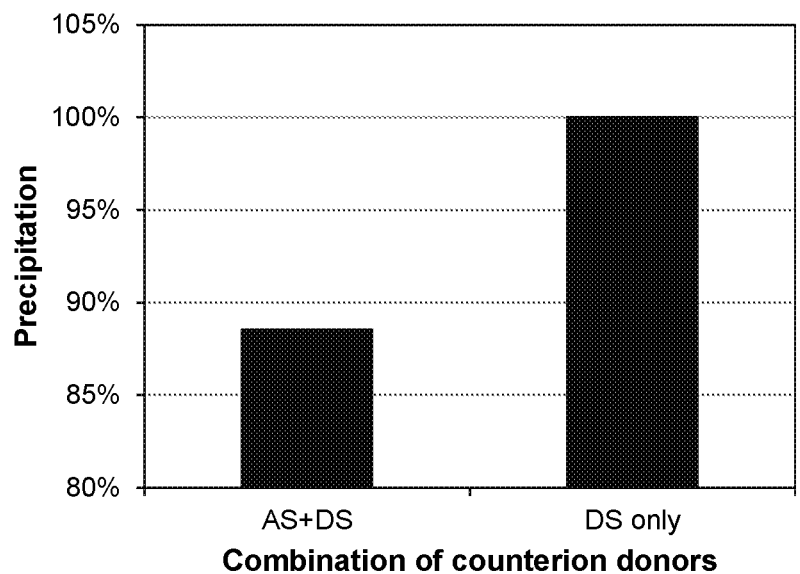
FIG. 7 shows the percentage of free-form vinorelbine in the precipitation study examining the interaction of vinorelbine with combination of the monovalent counterion donor and the polyvalent counterion donor or the polyvalent counterion donor alone.

In the groups where vinorelbine solution and liposomes were mixed with dextran sulfate alone, the percentage of remaining free-form vinorelbine decreased as the concentration of dextran sulfate increased. At an equivalent DS concentration of 15 mM, only 5.4% of free-form vinorelbine was measured. The capability of drug release at this DS concentration was found to be very poor, as almost all of the vinorelbine was tightly associated with DS. On the other hand, in the composition where vinorelbine solution and liposomes were mixed with ammonium sulfate alone (AS=200 mM, DS=0 mM), almost no precipitation was observed (97.6% of free-form remaining), indicating that the precipitation capability of ammonium sulfate alone was negligible. However, when vinorelbine solution and liposomes were combined with both ammonium sulfate and dextran sulfate, the ammonium sulfate resulted in an enhancement of free-form vinorelbine (as compared to DS alone), to an extent of up to 10.2% (21.2%−11.0%=10.2%, at DS of 39.35 mEq/L). Such difference can be recognized as an adjustment of drug release by ammonium sulfate (FIG. 7). The amount of the polyvalent counterions suitable for forming a precipitate that retains vinorelbine inside the liposomes was found to be from 5.27 mEq/L to 118.05 mEq/L, as shown in Table 12.

TABLE 12

Precipitation of vinorelbine with monovalent counterion donors and polyvalent counterion donors

| Counterion donors and equivalent concentration after mixing with VNB solution | AS (mM) | DS (mEq/L) | Percentage of free-form VNB remaining |
|---|---|---|---|
| AS = 200 mM, DS = 0 mM | 200 | 0 | 97.6% |
| AS = 200 mM, DS = 0.67 mM | 200 | 5.27 | 83.3% |
| AS = 200 mM, DS = 2.5 mM | 200 | 19.68 | 59.0% |
| AS = 200 mM, DS = 5 mM | 200 | 39.35 | 21.2% |
| AS = 200 mM, DS = 15 mM | 200 | 118.05 | 5.7% |
| AS = 0 mM, DS = 0 mM | 0 | 0 | 100.7% |
| AS = 0 mM, DS = 0.67 mM | 0 | 5.27 | 87.1% |
| AS = 0 mM, DS = 2.5 mM | 0 | 19.68 | 54.0% |
| AS = 0 mM, DS = 5 mM | 0 | 39.35 | 11.0% |
| AS = 0 mM, DS = 15 mM | 0 | 118.05 | 5.4% |

Abbreviations: VNB: Vinorelbine; AS: Ammonium sulfate; DS: Dextran sulfate.

Example 12: Adjustable Retention Profile Assayed by Precipitation Effect of Irinotecan with Mono- and Polyvalent Counterion Donor Combinations Various compositions were prepared by mixing 60 mg/mL of irinotecan solution and liposomes with 1 mM to 22.5 mM of dextran sulfate (molecular weight 1,600), or with 300 mM of ammonium sulfate and 1 mM to 22.5 mM of dextran sulfate (molecular weight 1,600), followed by vigorous agitation by vortex and centrifugation at 21,460×g for 30 minutes to separate insoluble precipitate from free-form irinotecan. The volume ratio for mixing the irinotecan solution and the counterion donor solution was 1:2, with the final equivalent counterion donor concentrations shown in Table 13.

Figure 8:
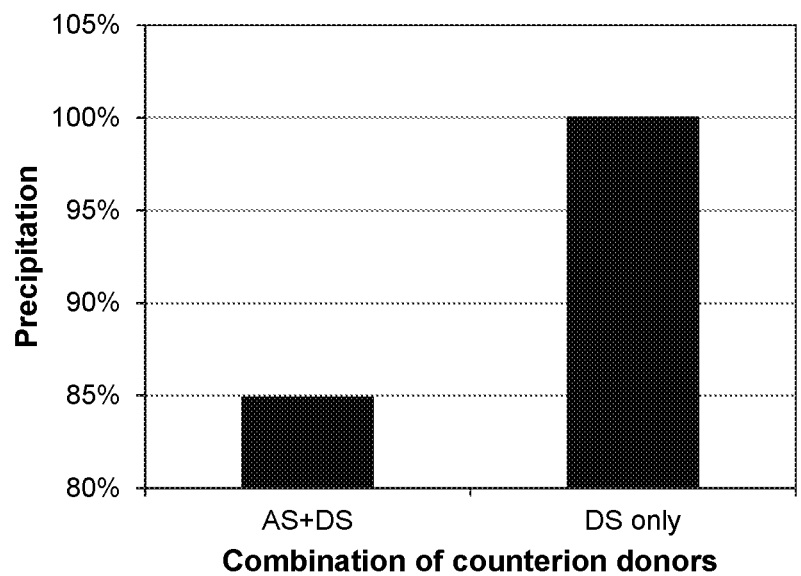
FIG. 8 shows the percentage of free form irinotecan in the precipitation study examining the interaction of irinotecan with the combination of the monovalent counterion donor and the polyvalent counterion donor or the polyvalent counterion alone.

In the groups where irinotecan solution and liposomes were mixed with dextran sulfate alone, the percentage of remaining free-form irinotecan decreased as the concentration of dextran sulfate increased. At an equivalent DS concentration of 15 mM, only 3.8% of free-form irinotecan was measured. The capability of drug release at such DS concentration was found to be very poor, as almost all of the irinotecan was tightly associated with DS. On the other hand, in the composition where irinotecan solution and liposomes were mixed with ammonium sulfate alone (AS=200 mM, DS=0 mM), almost no precipitation was observed (101.1% of free form remaining), indicating that the precipitation capability of ammonium sulfate alone was negligible. However, when irinotecan solution and liposomes were combined with both ammonium sulfate and dextran sulfate, ammonium sulfate resulted in an enhancement of free-form irinotecan (as compared to with DS alone), to an extent of up to 11% (38.3%−27.3%=11%, at DS of 19.68 mEq/L). Such difference can be recognized as an adjustment of drug release by ammonium sulfate (FIG. 8). The amount of the polyvalent counterions suitable for forming a precipitate that retains irinotecan inside the liposomes was found to be from 5.27 mEq/L to 118.05 mEq/L as in Table 13.

TABLE 13

Precipitation study examining irinotecan with monovalent counterion donors and polyvalent counterion donors

| Counterion donors and equivalent concentration after mixing with irinotecan solution | AS (mM) | DS (mEq/L) | Percentage of free-form CPT11 remaining |
|---|---|---|---|
| AS = 200 mM, DS = 0 mM | 200 | 0 | 101.1% |
| AS = 200 mM, DS = 0.67 mM | 200 | 5.27 | 83.8% |

TABLE 13-continued

Precipitation study examining irinotecan with monovalent counterion donors and polyvalent counterion donors

| Counterion donors and equivalent concentration after mixing with irinotecan solution | AS (mM) | DS (mEq/L) | Percentage of free-form CPT11 remaining |
|---|---|---|---|
| AS = 200 mM, DS = 1.6 mM | 200 | 12.59 | 59.4% |
| AS = 200 mM, DS = 2.5 mM | 200 | 19.68 | 38.3% |
| AS = 200 mM, DS = 5 mM | 200 | 39.35 | 9.7% |
| AS = 200 mM, DS = 15 mM | 200 | 118.05 | 9.0% |
| AS = 0 mM, DS = 0 mM | 0 | 0 | 103.4% |
| AS = 0 mM, DS = 0.67 mM | 0 | 5.27 | 82.0% |
| AS = 0 mM, DS = 1.6 mM | 0 | 12.59 | 50.9% |
| AS = 0 mM, DS = 2.5 mM | 0 | 19.68 | 27.3% |
| AS = 0 mM, DS = 5 mM | 0 | 39.35 | 2.3% |
| AS = 0 mM, DS = 15 mM | 0 | 118.05 | 3.8% |

Abbreviations: CPT11: Irinotecan; AS: Ammonium sulfate; DS: Dextran sulfate.

When ranges are used herein for physical properties, such as molecular weight, or for chemical properties, such as chemical formulae, all combinations and subcombinations of ranges for specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is therefore intended that the appended claims cover all such equivalent variations that fall within the spirit and scope of the invention.

What is claimed is:

1. A liposome for delivery of a toxic amphipathic anti-cancer therapeutic agent, comprising:
a particle-forming component selected from the group consisting of (i) phospholipid and (ii) a mixture of at least one phospholipid and cholesterol;
sodium dextran sulfate at an amount ranging from about 0.1 mM to about 3 mM;
sulfate anion at an amount ranging from about 100 mM to about 500 mM; and
an ammonium compound,
wherein the dextran sulfate of the sodium dextran sulfate has a molecular weight of about 1,000 Daltons to about 20,000 Daltons.

2. The liposome of claim 1, wherein the ammonium compound is $NR_4^+$, wherein each R is independently H or an organic residue.

3. A composition comprising the liposome of claim 1 and a toxic amphipathic anti-cancer therapeutic agent, a derivative thereof, or a pharmaceutically acceptable salt thereof.

* * * * *